United States Patent
Vaarbroe et al.

(10) Patent No.: US 9,265,664 B2
(45) Date of Patent: Feb. 23, 2016

(54) HEARING AID EAR PLUG WITH AN EXTRACTION CORD

(75) Inventors: Klaus Henrik Vaarbroe, Skovlunde (DK); Peter Nordland Jensen, Kastrup (DK)

(73) Assignee: Widex A/S, Lynge (DK)

( * ) Notice: Subject to any disclaimer, the term of this patent is extended or adjusted under 35 U.S.C. 154(b) by 488 days.

(21) Appl. No.: 13/551,986

(22) Filed: Jul. 18, 2012

(65) Prior Publication Data

US 2013/0014768 A1    Jan. 17, 2013

Related U.S. Application Data

(63) Continuation-in-part of application No. PCT/EP2010/050570, filed on Jan. 19, 2010.

(51) Int. Cl.
| | | |
|---|---|---|
| *A61F 11/08* | (2006.01) | |
| *H04R 25/00* | (2006.01) | |
| *H04R 31/00* | (2006.01) | |

(52) U.S. Cl.
CPC .............. *A61F 11/08* (2013.01); *H04R 25/652* (2013.01); *H04R 25/658* (2013.01); *H04R 31/006* (2013.01); *A61F 2011/085* (2013.01); *H04R 2460/17* (2013.01); *Y10T 29/49572* (2015.01)

(58) Field of Classification Search
USPC .......... 180/129–130, 134–135; 128/864–865, 128/867; D24/106, 174; D29/112; 2/209, 2/68, 918; 381/72, 123, 156, 324
See application file for complete search history.

(56) References Cited

U.S. PATENT DOCUMENTS

| | | | |
|---|---|---|---|
| 4,716,985 A | | 1/1988 | Haertl |
| 5,881,729 A | * | 3/1999 | Castillo .......................... 128/864 |
| 6,048,305 A | | 4/2000 | Bauman et al. |
| 6,148,821 A | * | 11/2000 | Falco .............................. 128/864 |
| 6,938,622 B2 | * | 9/2005 | Huang ........................... 128/864 |
| 2005/0229938 A1 | * | 10/2005 | Jenkins, Jr. .................... 128/854 |
| 2008/0279405 A1 | | 11/2008 | Isogi et al. |
| 2009/0074221 A1 | * | 3/2009 | Westermann ................. 381/327 |

FOREIGN PATENT DOCUMENTS

| | | |
|---|---|---|
| EP | 1629808 A1 | 3/2006 |
| JP | 62-285600 A | 12/1987 |
| JP | 6-70398 | 3/1994 |
| JP | 11-507792 | 7/1999 |
| WO | 97/00593 A1 | 1/1997 |

(Continued)

OTHER PUBLICATIONS

Japanese Office Action for Japanese Patent Application No. 2012-548356 dated Sep. 3, 2013.

(Continued)

*Primary Examiner* — Ophelia A Hawthorne
(74) *Attorney, Agent, or Firm* — Sughrue Mion, PLLC

(57) ABSTRACT

An ear plug (1) for a hearing aid is made of a resilient material and provided with an extraction cord (4) for providing a grip by which a user can pull the ear plug (1) out of an ear canal. The extraction cord (4) is arranged partly in the resilient material and partly outside the ear plug. A securing bulge (6) is arranged on the part of the extraction cord arranged in the resilient material, in order to secure the position of the extraction cord in the resilient material. The extraction cord is bonded to the resilient material. The invention further concerns a method for manufacturing the ear plug.

12 Claims, 3 Drawing Sheets

(56) References Cited

FOREIGN PATENT DOCUMENTS

| WO | 98/51125 A1 | 11/1998 |
| WO | 2007/077605 A1 | 7/2007 |
| WO | 2010/040419 A1 | 4/2010 |

OTHER PUBLICATIONS

International Search Report for PCT/EP2010/050570 dated Mar. 15, 2010.

\* cited by examiner

HEARING AID EAR PLUG WITH AN EXTRACTION CORD

The present application is a continuation-in-part of application PCT/EP2010050570, filed on Jan. 19, 2010, in Europe and published as WO 2011088887 A1.

BACKGROUND OF THE INVENTION

1. Field of the Invention

The present invention relates to hearing aids. The invention further relates to methods of making hearing aids. The invention more specifically concerns an ear plug for a hearing aid, which ear plug is made of a resilient material and is provided with an extraction cord for pulling the ear plug out of an ear canal. The invention still further relates to a method for manufacturing an ear plug One general class of hearing aids comprises the behind-the-ear type with a housing placed behind the ear and an ear mould or ear plug arranged in the ear canal of the hearing aid user. The sound signal is picked up, amplified and processed in the behind-the-ear unit suitably to compensate the user's hearing deficiency, and transferred to the ear plug as an acoustic signal through a sound tube or as an electrical signal through a wire to a receiver or loudspeaker arranged in the ear mould.

For many hearing aid users a soft, pliable and resilient ear mould will be preferred as this will more easily adapt to the shape of the auditory canal wall, and thereby be more comfortable to the hearing aid user. Furthermore, a soft and resilient outer surface will make continuous adaptation to changes in the geometry of the ear canal feasible. Such changes in geometry may be caused e.g. when the hearing aid user is chewing or yawning.

2. The Prior Art

If the resilient ear plug is also custom fitted to the individual shape of the auditory canal this will be the optimum solution as this will minimize any localized mechanical pressure in the auditory canal. The custom fitted resilient ear plug may be manufactured according to the method described in PCT/EP2008/063663, published as WO-A1-2010040419.

In order to be able to remove such earplugs from the ear canal an extraction cord is often provided. An extraction cord projects out of the ear plug, and just outside, or close to the outside, of the ear canal, such that the person wearing the hearing aid can grab the extraction cord between two fingers and pull out the earplug from the ear canal.

WO-A1-98/51125 discloses an ear mould for a hearing aid, where the ear mould is made of a soft and pliable material such as silicone. The ear mould is provided with fins for obtaining a comfortable fit to the ear canal and for holding the ear mould in the ear by both friction and by mechanical locking. The ear mould is further provided with an extraction cord for pulling out the ear mould.

SUMMARY OF THE INVENTION

The problem with the known solutions of soft and pliable ear plugs or ear moulds provided with extraction cords is, that it is difficult to make a sufficiently strong construction where the extraction cord will not either break off, or be drawn out of the soft and pliable material.

In a first aspect, the invention provides an ear plug for a hearing aid, comprising a resilient ear mould and an extraction cord for providing a grip by which a user can pull the ear plug out of an ear canal, said extraction cord being arranged partly in the ear mould and partly outside the ear mould, wherein a securing bulge is arranged on the part of the extraction cord arranged in the ear mould, in order to secure the position of the extraction cord in the ear mould, wherein the extraction cord is bonded to the ear mould, and wherein said securing bulge is provided with either a first color marking for indicating that the ear plug is to be used in the right ear or a second color marking for indicating that the ear plug is to be used in the left ear.

This solution has the advantage of providing the ear plug with an extraction cord which is very strong and is not easily drawn out of the resilient material. The bonding may be achieved either by a suitable glue, or by hardening the resilient material after placing and holding the extraction cord in the correct position whereby the resilient material will bond to the extraction cord.

Providing the securing bulge with either a first colour marking for indicating that the ear plug is to be used in the right ear, or with a second colour marking for indicating that the ear mould is to be used in the left ear, is a simple and durable way of marking the ear plugs, and making them easily discernable to the hearing aid user. Preferably, the resilient material is at least partially transparent in order for the colour to be visible when the ear plug is not in the ear canal.

In a further embodiment the extraction cord is provided with holding means in order to avoid the fingers slipping when pulling the extraction cord. This makes it easier to get a good grip by the fingers on the extraction cord, and the length of the extraction cord can at the same time be kept at a minimum. Preferably, the holding means are droplet shaped or substantially droplet shaped and arranged at the end of said extraction cord. Such a shape will be easy to manufacture and avoids any edges which could bother the skin.

In a further embodiment the securing bulge is cone shaped or substantially cone shaped with the axis of the cone being parallel or substantially parallel with the length direction of the extraction cord, and wherein the part of the cone having the largest cross sectional area is facing the end of the extraction cord extending out of the resilient material. This is also the pulling direction or the direction out of the ear. This shape has been found to be the optimal shape both for entering the extraction cord through a narrow hole and for avoiding the extraction cord being pulled out of the resilient ear plug material.

In a further embodiment the extraction cord has a total length of 15-25 mm, preferably 18-22 mm. This range has been found to be suitable for easily getting a grip with the fingers in the extraction cord without the extraction cord being more visible than necessary.

In a second aspect, the invention provides a method of manufacturing a resilient ear plug, comprising the steps of providing a material for a resilient ear mould, forming a resilient ear mould from said material, providing an extraction cord, said extraction cord being provided with a bulge on part of its length, said bulge being provided with either a first color marking for indicating that the ear plug is to be used in the right ear or with a second color marking for indicating that the ear plug is to be used in the left ear, entering said extraction cord partly into said ear mould with the bulge on the part of the extraction cord entered into said ear mould, and with an end of the extraction cord extending outside said ear mould, and bonding said extraction cord to said ear mould.

By this method an ear plug with a mechanical strong extraction cord is manufactured.

In a further embodiment the method comprises the step of providing a hole in said resilient material for said extraction cord, before entering the extraction cord into said resilient material. Preferably, the extraction cord is then bonded by adding a suitable glue. Such glue is preferably entered in the hole before the extraction cord, or applied directly to the extraction cord. In an alternative embodiment of the method the extraction cord is entered into the resilient ear mould material before this material is hardened. Preferably, the extraction cord is then bonded by the hardening of the ear mould material.

In a further embodiment of the method the extraction cord including the bulge is manufactured by injection molding. This facilitates a fast and accurate manufacturing.

In a third aspect, the invention provides a method of manufacturing a hearing aid, comprising the steps of providing a material for a resilient ear mould, forming a resilient ear mould from said material, providing an open space in said ear mould, providing an extraction cord, said extraction cord being provided with a bulge on part of its length, entering said extraction cord partly into said ear mould with the bulge on the part of the extraction cord entered into said ear mould, and with an end of the extraction cord extending outside said ear mould, bonding said extraction cord to said ear mould, securing a receiver in said space, providing a behind-the-ear housing part, and connecting said receiver by electric wires to said behind-the-ear housing part.

BRIEF DESCRIPTION OF THE DRAWINGS

Embodiments of the invention will now be explained in further detail with reference to the figures.

DETAIL DESCRIPTION OF THE INVENTION

Figure 1:
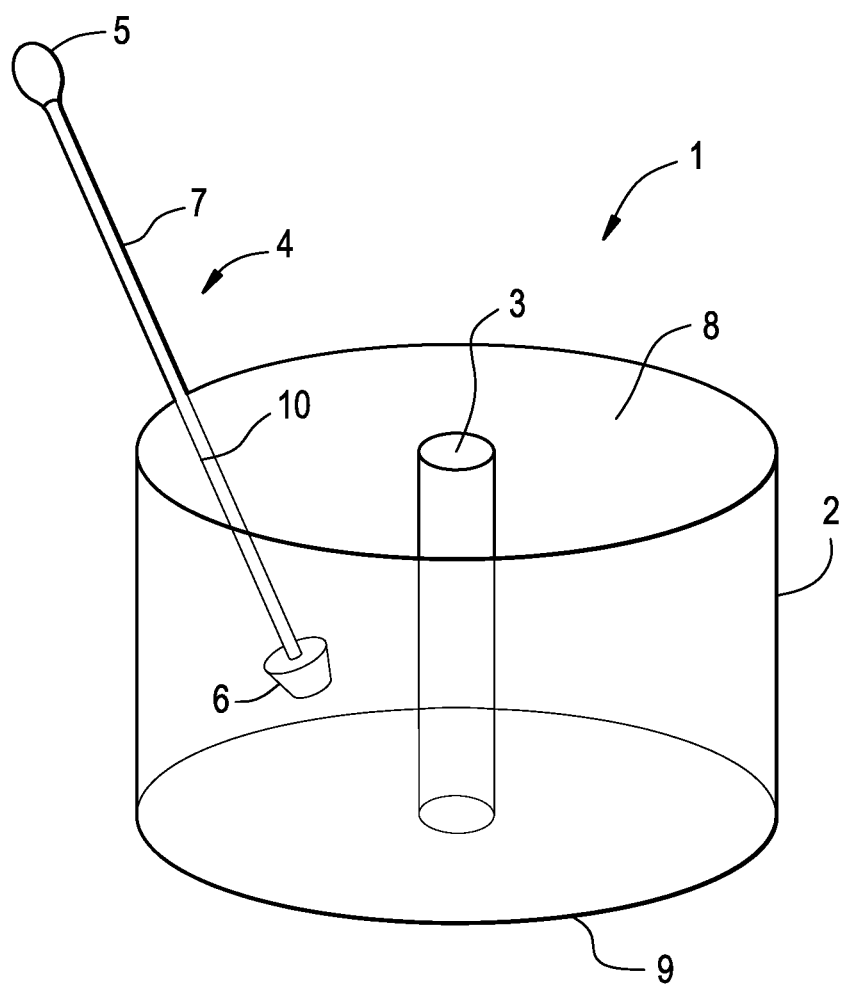

FIG. 1 illustrates an ear plug with an extraction cord; and

Figure 2A:
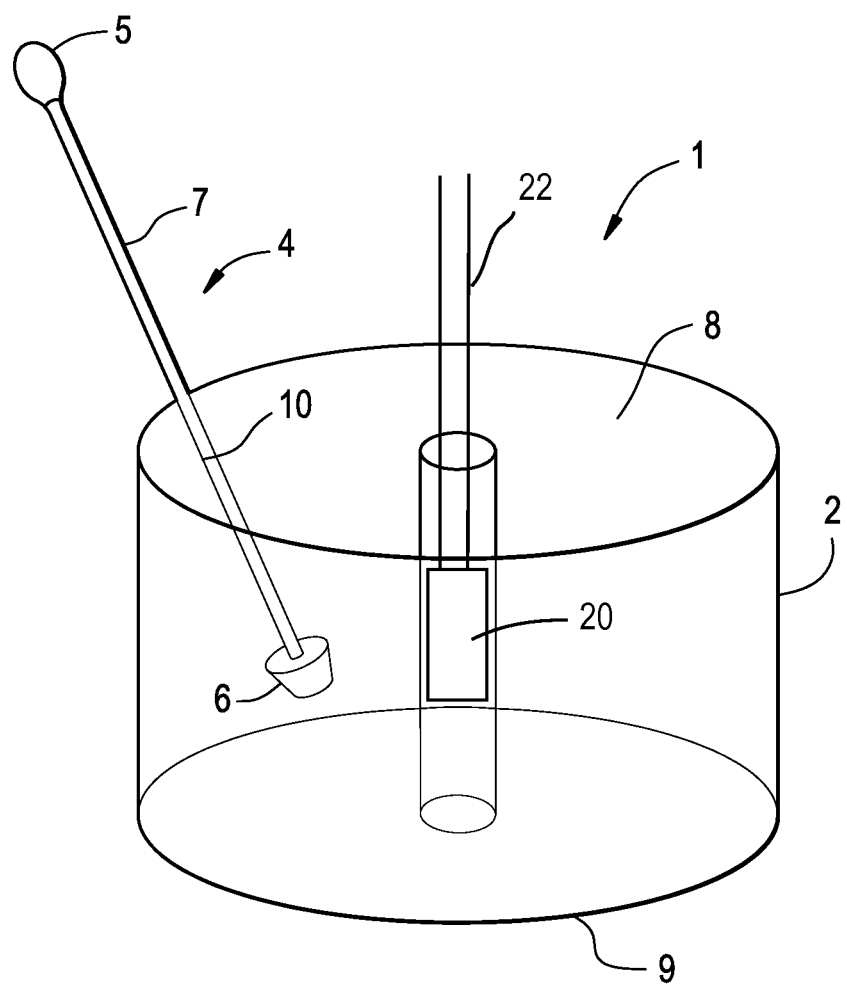
Figure 2B:
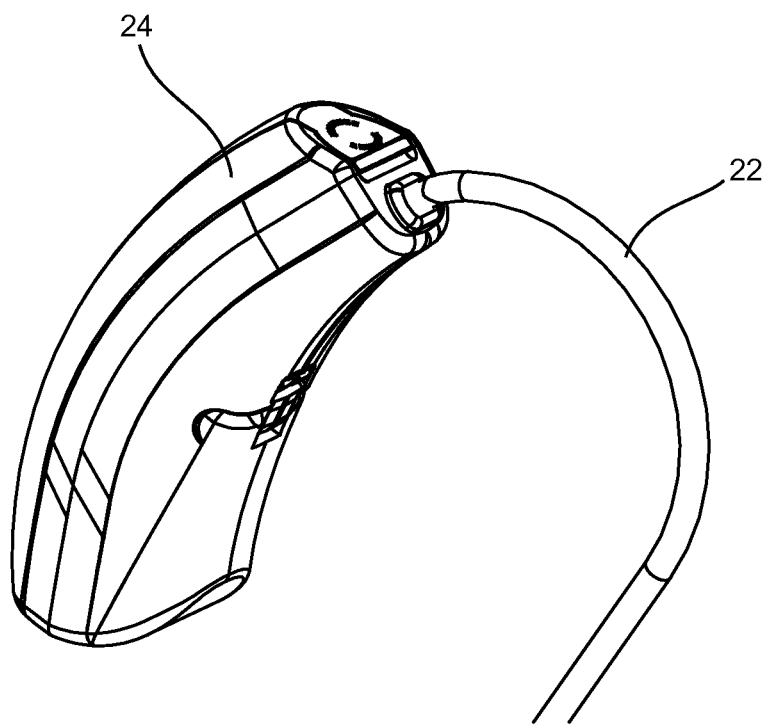

FIGS. 2A and 2B illustrate an embodiment of the ear plug of FIG. 1 having a receiver in the ear plug connected to a behind-the-ear housing.

FIG. 1 shows an embodiment of an ear plug 1 with an extraction cord 4, where the ear plug part 2 has been custom fitted to a specific ear canal. The ear plug 2 has been made in a soft, pliable and resilient material, such as a silicone. The ear plug 2 is provided with an open space 3 or hole for arranging the receiver or for connecting a sound tube. This space goes through the earplug connecting the end outer surface 8 facing the open end of the ear canal with the inner surface 9 facing the ear drum when the ear plug is arranged in the ear canal. A receiver may be secured in this space, as shown by receiver 20 in FIG. 2A. It is connected by electrical wires 22 to the behind-the-ear housing part 24 of the hearing aid, as shown in FIG. 2B. When the hearing aid is of the type having the receiver in the behind the ear part, the sound is guided to the ear plug through a sound tube which ends in the space 3 and is secured to the ear plug 1.

An extraction cord 4 is important in order to avoid that the hearing aid user pulls out the ear plug by drawing on the electrical wire or on the sound tube. If this is done repeatedly this may lead to failure of these components.

The extraction cord 4 comprises the cord part or shaft part 7, holding means in the form of a knob 5 and a bulge part in the form of a barb or a cone shaped bulge part 6. The bulge part 6 has to be arranged inside the ear plug material, when the extraction cord is placed at a point 10 in the ear plug material. The bulge part could have other shapes than cone shaped. The important thing is that it is easy to insert the extraction cord into a hole in the ear plug material, and that the bulge part, by its shape and by bonding or gluing, resists being drawn out of the ear plug material. The cord part 7 could be provided with more than one bulge part, e.g. two cones instead of one. However, there is usually not much space in the ear plug material, and therefore the volume of the extraction cord should also be kept at a minimum in order not to reduce the stability or strength of the ear plug material.

In an example of the extraction cord it is made of polyamide or nylon, and the shaft or cord part 7 has a diameter of about 0.5 mm and a length of about 16 mm. The total length of the extraction cord is about 20 mm, where the knob 5 has a diameter of about 2 mm and the cone 6 has a length along a longitudinal axis of the cord of about 2 mm. The maximum diameter of the cone is about 2 mm. In practice the extraction cord will be manufactured in different lengths in order to fit into different sizes of ear plugs.

The extraction cord may be moulded in one step with the three parts mentioned included. Alternatively the cord part 7 and the knob 5 are made in a first step, and the cone 6 is made in a second step, and subsequently attached to the cord part 7, e.g. by gluing. This makes it simpler to manufacture the cone in a different colour, and even in a different material. The colour of the cone 6 will usually be visible through the more or less transparent material of the ear plug part 2. The cord part 7 and the knob 5 of the extraction cord 4 will usually also be made transparent in order to make the ear plug as such less visible. If the cone 6 in each of two ear plugs for the same person is made in different colours, e.g. red for the cone in the right ear plug and blue for the cone in the left ear plug, it will be much easier for the person to remember which ear plug has to be placed in which ear.

The advantage of colouring the cones is, that the colouring is more durable than would be the case with colouring of a silicone surface, that the colouring of the cone is not subject to wear and that the logistics are simpler by relying on a standard, non-customized component for colour indication.

The resilient material of the ear plug is preferably silicone. A preferred silicone is the Biopor, which is biocompatible. However, other resilient materials, such as soft acrylic may also be applied. The ear plug is usually cast in a mould formed on the basis of data representing the shape and size of the ear canal of the person going to use the hearing aid. Depending on the type of silicone applied, different methods may be used for hardening the silicone. Examples of methods for hardening are heat, ultraviolet radiation and mixing of a two-component silicone. The resilient material should preferably be bio-compatible. A resilient material is understood as being a material resuming its original shape after compression.

The extraction cord is preferably manufactured by injection moulding but other manufacturing methods as might be suggested by those skilled in the art may be applied as well.

The extraction cord 4 can be placed in the ear plug material in different ways. In one way the resilient ear plug material is hardened first, and a hole for the extraction cord is made, e.g. by drilling. The diameter of this hole will be slightly larger than the diameter of the shaft or cord part 7, but smaller than the largest diameter of the cone 6. This will make the extraction cord easy to enter into the material, leave sufficient space for the glue, and make the extraction cord difficult to draw out.

Another way to arrange the extraction cord in the ear plug material is to arrange it in the material before this is hardened. In that case gluing will not be necessary, because the material will bond to the extraction cord while hardening.

We claim:

1. A method of manufacturing a resilient ear plug, comprising the steps of
   providing a material for a resilient ear mould,
   forming a resilient ear mould from said material, said resilient ear mould being at least partially transparent, providing an extraction cord, said extraction cord being provided with a bulge on part of its length, said bulge being provided with either a first color marking for indicating that the ear plug is to be used in a right ear or with a second color marking for indicating that the ear plug is to be used in a left ear, entering said extraction cord partly into said ear mould with the bulge on the part of the extraction cord entered into said ear mould such that said bulge is visible through a partially transparent portion of said ear mould, and with an end of the extraction cord extending outside said ear mould, and bonding said extraction cord to said ear mould.

2. The method according to claim 1, wherein said extraction cord is entered into said ear mould before the material is hardened.

3. The method according to claim 2, wherein said extraction cord is bonded to said ear mould by the hardening of said material.

4. The method according to claim 1, further comprising the step of providing a hole in said ear mould for said extraction cord, before entering the extraction cord into said ear mould.

5. The method according to claim 1, wherein said extraction cord is bonded to said ear mould by adding a suitable glue.

6. The method according to claim 1, wherein said extraction cord including said bulge is manufactured by injection molding.

7. An ear plug for a hearing aid, comprising a resilient ear mould and an extraction cord for providing a grip by which a user can pull the ear plug out of an ear canal, said extraction cord being arranged partly in the ear mould and partly outside the ear mould, wherein a securing bulge is arranged on a part of the extraction cord arranged in the ear mould within said resilient material, in order to secure a position of the extraction cord in the ear mould, wherein the extraction cord is bonded to the ear mould, and wherein said securing bulge is provided with either a first color marking for indicating that the ear plug is to be used in a right ear or a second color marking for indicating that the ear plug is to be used in a left ear, the resilient material being at least partially transparent in order for the color to be visible.

8. The ear plug according to claim 7, wherein said extraction cord is provided with holding means for providing a grip for one or more fingers for pulling the extraction cord to pull out the ear plug.

9. The ear plug according to claim 8, wherein said holding means are droplet shaped or substantially droplet shaped and arranged at an end of said extraction cord arranged outside said ear mould.

10. The ear plug according to claim 7, wherein said securing bulge is cone shaped or substantially cone shaped with the axis of the cone being parallel or substantially parallel with a length direction of the extraction cord, and wherein a part of the cone having the largest cross sectional area is facing the end of the extraction cord arranged outside said ear mould.

11. A method of manufacturing a hearing aid, comprising the steps of
providing a material for a resilient ear mould,
forming a resilient ear mould from said material, said resilient ear mould being at least partially transparent,
providing an open space in said ear mould,
providing an extraction cord, said extraction cord being provided with a bulge on part of its length,
entering said extraction cord partly into said ear mould with the bulge on the part of the extraction cord entered into said ear mould such that said bulge is visible through a transparent part of said ear mould, and with an end of the extraction cord extending outside said ear mould,
bonding said extraction cord to said ear mould,
securing a receiver in said open space,
providing a behind-the-ear housing part, and
connecting said receiver by electric wires to said behind-the-ear housing part.

12. The method according to claim 11, comprising providing said bulge with either a first color marking for indicating that the ear plug is to be used in a right ear or with a second color marking for indicating that the ear plug is to be used in a left ear.

* * * * *